United States Patent
Koike et al.

(10) Patent No.: US 7,223,882 B2
(45) Date of Patent: May 29, 2007

(54) PROCESS FOR PRODUCING TRITERPENE DERIVATIVE

(75) Inventors: Haruo Koike, Tokushima (JP); Katsuo Oda, Amagasaki (JP); Yutaka Nishino, Amagasaki (JP); Makoto Kakinuma, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 336 days.

(21) Appl. No.: 10/508,476

(22) PCT Filed: Mar. 18, 2003

(86) PCT No.: PCT/JP03/03248

§ 371 (c)(1),
(2), (4) Date: Sep. 21, 2004

(87) PCT Pub. No.: WO03/080643

PCT Pub. Date: Oct. 2, 2003

(65) Prior Publication Data

US 2005/0143596 A1      Jun. 30, 2005

(30) Foreign Application Priority Data

Mar. 22, 2002    (JP)  .............................. 2002-080364

(51) Int. Cl.
  C07C 261/00    (2006.01)
  C07C 69/74     (2006.01)
  C07C 229/00    (2006.01)
  C07C 61/12     (2006.01)
  C07D 303/00    (2006.01)

(52) U.S. Cl. .................. 560/115; 560/116; 562/455; 562/498; 549/332

(58) Field of Classification Search ................ 560/115, 560/116; 562/455, 498; 549/332
    See application file for complete search history.

(56) References Cited

U.S. PATENT DOCUMENTS 5,248,807 A    9/1993  Fujimoto et al.

(Continued)

FOREIGN PATENT DOCUMENTS

EP    0 628 569    12/1994

(Continued)

OTHER PUBLICATIONS

J. Org. Chem., (1997), 62(4), p. 960-6.

(Continued)

*Primary Examiner*—J. Parsa
(74) *Attorney, Agent, or Firm*—Wenderoth, Lind & Ponack, L.L.P.

(57) ABSTRACT

A process for a preparation of Compound (V), a pharmaceutically acceptable salt or a solvate thereof, said process comprising the steps represented by the following formula:

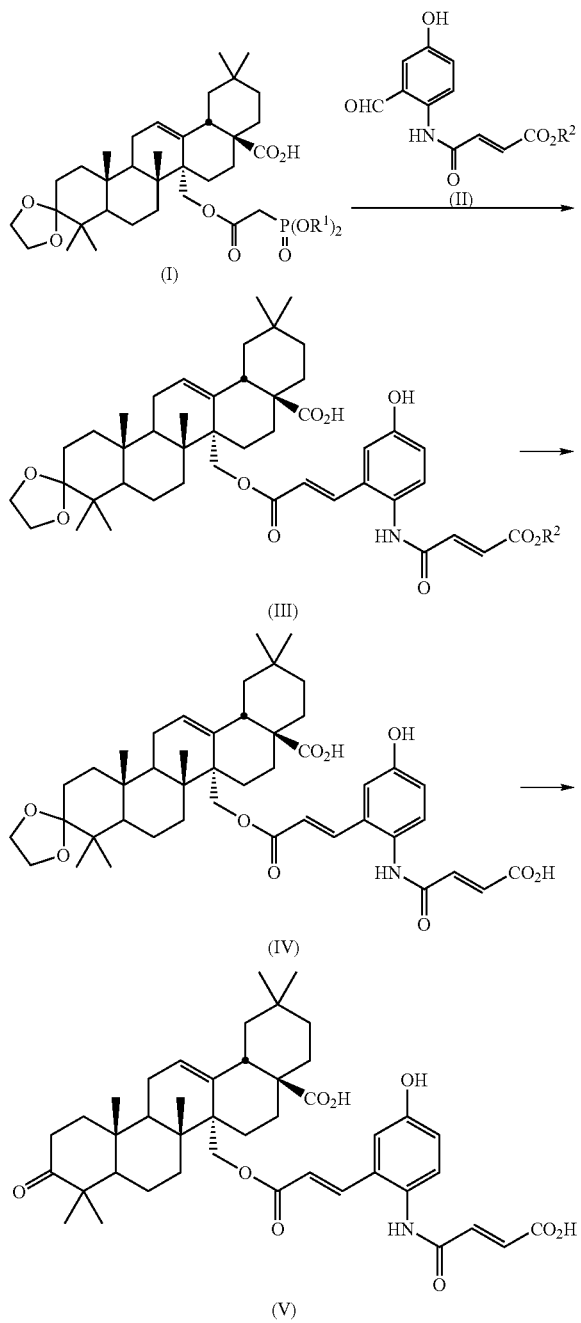

wherein $R^1$ and $R^2$ are each independently C1–C8 alkyl.

14 Claims, 1 Drawing Sheet

U.S. PATENT DOCUMENTS 5,463,107 A    10/1995    Konoike et al.
5,587,505 A    12/1996    Konoike et al.

FOREIGN PATENT DOCUMENTS

| | | |
|---|---|---|
| JP | 6-345716 | 12/1994 |
| JP | 7-101956 | 4/1995 |
| JP | 7-316188 | 12/1995 |
| WO | 92/12991 | 8/1992 |
| WO | 97/27314 | 7/1997 |

OTHER PUBLICATIONS

Organic Process Research & development, (1999), 3(5), p. 347-51.

Figure 1

PROCESS FOR PRODUCING TRITERPENE DERIVATIVE

This application is a U.S. National Stage of International Application No. PCT/JP03/03248 filed Mar. 18, 2003.

TECHNICAL FIELD

The present invention relates to processes for triterpene derivatives which are useful as an endothelin receptor antagonist and the like, especially a compound of the formula:

(V)

a pharmaceutically acceptable salt or solvate thereof (hereinafter referred to as Compound (V)).

BACKGROUND ART

Compound (V) is an endothelin receptor antagonist and useful for treating various circulatory system diseases such as hypertension, ischemic disorders, cerebral circular disorders, renal disorders, circular insufficiency of various organs, asthma, stroke, cerebral infarction, cerebral edema and the like (Patent Literature 1, Patent Literature 2 etc.). A process for preparing oleanolic acid derivatives, which are intermediates of Compound (V), such as myricerone etc., is disclosed in Patent Literature 3. Additionally, a process for preparing Compound (V) using an oleanolic acid is disclosed in Non-Patent Literature 1 and Non-Patent Literature 2 etc. However, processes described in these literatures need an isolation process of intermediates, different reagents or solvents in each reaction step, environmental harmful reagents or the like and are not necessarily sufficient for industrial manufacturing processes.

A method for reduction of a nitro group of hydroxy-2-nitrobenzaldehyde to an amino group by catalytic reduction is described in Patent Literature 4, but in this method, a reduction process is conducted after an aldehyde group is protected as acetal.

Patent Literature 1 WO92/12991
Patent Literature 2 JP 7-53484 A
Patent Literature 3 JP 7-316188 A
Patent Literature 4 JP 7-1011956 A
Non-Patent Literature 1 Organic Process Research & Development, 1999, vol. 3, p.347–351
Non-Patent Literature 2 Journal of Organic Chemistry, 1997, vol.62, p.960–966

DISCLOSURE OF INVENTION

A development of efficient manufacturing mass-production process of Compound (V) or intermediates thereof has been desired.

BEST MODE FOR CARRYING OUT THE INVENTION

The inventors of the present invention studied for improvement of a process of Compound (V) and completed the following inventions.

(1) A process for a preparation of Compound (V), a pharmaceutically acceptable salt or a solvate thereof, said process comprising the steps of:

(Step 1) producing a solution containing Compound (III) by reacting Compound (I) with Compound (II) in the presence of a lithium reagent (A) in an organic solvent, (Step 2) producing a solution containing Compound (IV) by adding a lithium reagent (B) to the solution obtained by Step 1, and

(Step 3) adding an acid to the solution obtained by Step 2, represented by the formula:

-continued (III)

(IV)

(V)

wherein $R^1$ and $R^2$ are each independently C1–8 alkyl.

(2) A process for a preparation of Compound (V), a pharmaceutically acceptable salt or a solvate thereof comprising conducting the following steps in sequence:

(Step 1) dissolving Compound (I), Compound (II) and a lithium reagent (A) in an organic solvent, (Step 2) adding a lithium reagent (B), and (Step 3) adding an acid, represented by the formula:

wherein $R^1$ and $R^2$ are each independently C1–C8 alkyl.

(3) The process as described in the above (1) or (2) comprising isolating Compound (V), a pharmaceutically acceptable salt or a solvate thereof.

(4) The process as described in any one of the above (1) to (3) wherein the lithium reagent (A) is lithium chloride or lithium hydroxide and the lithium reagent (B) is lithium hydroxide.

(5) The process as described in any one of the above (1) to (4) wherein the organic solvent is N,N-dimethylformamide.

(6) A process for a preparation of Compound (II), a pharmaceutically acceptable salt or a solvate thereof, said process comprising the steps of:

(Step 1) producing a solution containing Compound (VII) by reducing Compound (VI) in the presence of Pd—C, and (Step 2) reacting Compound (VII) in the solution obtained by Step 1 with Compound (VIII), represented by the formula:

wherein $R^2$ is C1–C8 alkyl.

(7) The process as described in the above (6) wherein Step 2 is conducted at a pH value in the range from 1 to 7.

(8) The process as described in the above (6) wherein Step 2 is conducted in the presence of N,N-dimethylaniline.

(9) A process for a preparation of Compound (V), a pharmaceutically acceptable salt or a solvate thereof, said process comprising the steps of:

(Step 1) producing a solution containing Compound (IV) by reacting Compound (I) with Compound (II') in the presence of a base in an organic solvent and water, and

(Step 2) adding an acid to the solution obtained by Step 1, represented by the formula:

wherein $R^1$ is C1–C8 alkyl and $R^3$ is hydrogen or C1–C8 alkyl.

(10) A process for a preparation of Compound (V), a pharmaceutically acceptable salt or a solvate thereof comprising conducting the following steps in sequence:

(Step 1) dissolving Compound (I), Compound (II') and a base in an organic solvent and water, and (Step 2) adding an acid, represented by the formula:

wherein $R^1$ is C1–C8 alkyl and $R^3$ is hydrogen or C1–C8 alkyl.

(11) The process as described in the above (9) or (10) comprising isolating Compound (V), a pharmaceutically acceptable salt or a solvate thereof.

(12) The process as described in any one of (9) to (11) wherein the base is lithium hydroxide, sodium hydroxide or potassium hydroxide.

(13) A crystal of Compound (I-1) of the formula:

(I-1)

wherein $R^1$ is ethyl.

(14) A process for a preparation of Compound(V) comprising removing endotoxin by dissolving Compound (V) according to the above (1) in an organic solvent and washing with purified water.

(15) The process as described in the above (14) wherein the organic solvent is ethyl acetate.

A process for a preparation of Compound (V) using the above Compound (I) is explained as an embodiment of the present invention.

(Method A, Step 1)

In this step, Compound (I), Compound (II) and Lithium reagent (A) are dissolved in an organic solvent. A solution containing Compound (III) is obtained by reacting Compound (I) with Compound (II) in the presence of Lithium reagent (A) in an organic solvent.

In the specification, "a solution" includes a homogeneous solution wherein Compound (III) is dissolved and a suspension wherein Compound (III) is not perfectly dissolved but suspended.

Hereinafter, "a solution" in the specification includes a suspension and "dissolution" also includes "suspension."

Compound (I) and a 3-keto derivative thereof can be produced in a similar manner to the methods described in the above Patent-Literature 3, Non-Patent Literature 1, Non-Patent Literature 2 etc., or the method using Horner-Emmons Reaction according to the above literatures. Compound (I) can be easily produced by protecting a 3-keto derivative with an ethylenedioxo group.

Compound (II) can be also produced by a similar method described in the above literatures.

"C1–C8 alkyl" represented by $R^1$ or $R^2$ includes a straight and a branched alkyl. Examples of "C1–C8 alkyl" are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl and isooctyl. Methyl or ethyl is preferable for $R^1$ and ethyl is more preferable. Methyl is preferable for $R^2$.

Examples of a-lithium reagent (A) are lithium chloride, lithium bromide, lithium hydroxide and lithium carbonate. Lithium chloride and lithium hydroxide are preferable. About 2.0 to 10.0 mole equivalent, preferably about 2.0 to 3.0 mole equivalent of a lithium reagent(A) relative to Compound (I) is used.

Examples of an organic solvent are N,N-dimethylformamide, diethyl ether, tetrahydrofuran, N,N-dimethylacetamide and ethylene glycol dimethyl ether. N,N-dimethylformamide is preferable.

The reaction temperature is generally about −20 to 60° C. and preferably about 10 to 20° C.

The reaction time is generally about 1 hour to 50 hours and preferably 6 hours to 24 hours.

The reaction may be performed in the presence of a base, if necessary. Examples of a base are DBU(1,8-diazabicyclo [5.4.6]undec-7-ene), trimethylamine, triethylamine, choline, procaine and ethanolamine, and DBU is preferable.

A solution containing Compound (III) is obtained by this step. Although Compound (III) may be isolated, it can be preferably used in a following step without isolation.

(Step 2)

In this step, a lithium reagent (B) is added to the reaction mixture obtained by Step 1. A solution containing Compound (IV) can be obtained by adding a lithium reagent (B) to the solution containing Compound (III) obtained by Step 1.

Examples of a lithium reagent (B) are lithium hydroxide and lithium carbonate, and lithium hydroxide is preferable. The amount of a lithium reagent (B) for this reaction is about 2.0 to 10.0 mole equivalent and preferably about 2.0 to 4.0 mole equivalent relative to Compound (II). The above lithium reagent (B) may be the same reagent as the lithium reagent (A) or different reagent from the lithium reagent (A).

Examples of an organic solvent are N,N-dimethylformamide, diethyl ether, tetrahydrofuran, N,N-dimethylacetamide and ethylene glycol dimethyl ether. The same solvent as used in Step 1 is preferable and more preferably N,N-dimethylformamide.

The reaction temperature is generally about −40 to 60° C., and preferably about −10 to 0° C.

The reaction time is generally about 0.1 hour to 10 hours, and preferably about 0.5 hour to 2.0 hours.

A solution containing Compound (IV) is obtained by this step. Although Compound (IV) may be isolated, it can be preferably used in the following step without isolation.

(Step 3)

In this step, an acid is added to the reaction mixture obtained by Step 2. Compound (V) is obtained by adding an acid to the solution containing Compound (IV) obtained by Step 2. Compound (V) can be isolated, preferably as crystals, by extracting, washing with water, crystallizing and the like according to the usual methods.

An acid is not particularly limited and any acid which can deprotect an ethylenedioxy group of Compound (IV) can be used. Examples of an acid are hydrochloric acid, hydrobromic acid, sulfuric acid, nitric acid, phosphoric acid, p-toluenesulfonic acid, methanesulfonic acid, formic acid, trifluoroacetic acid, maleic acid and oxalic acid, and hydrochloric acid is preferable. Amount of acid is about 4.5 to 15.0 mole equivalent, preferably about 7.0 to 9.0 mole equivalent relative to Compound (IV).

The reaction temperature is generally about 0 to 80° C., and preferably about 40 to 50° C.

The reaction time is generally 0.1 hour to 10 hours, and preferably about 1.0 hour to 2.0 hours.

According to the above steps, Compound (V) can be obtained by a one-pot reaction from Compound (I), preferably without isolating each of the intermediates. The same kind of base or solvent can be used in each of the steps. Therefore, the present processes are very useful for manufacturing processes.

(Method B)

Compound (V) can be obtained by conducting the following steps in sequence; dissolving Compound (I), Compound (II') and a base in an organic solvent and water, and adding an acid to the mixture. Compound (V) is obtained by the following steps; a step for reacting Compound (I) with Compound (II') in the presence of a base in an organic solvent and water to give a solution containing Compound (IV), and a step wherein the solution containing Compound (IV) is subjected to the reaction in the manner similar described in the above Method A, Step 3.

"C1–C8" alkyl represented by $R^3$ is the same as the above-mentioned $R^1$ or $R^2$.

Examples of a base is lithium hydroxide, sodium hydroxide and potassium hydroxide, and lithium hydroxide is preferable. Amount of the base is about 2.0 to 10.0 mole equivalent, and preferably about 2.0 to 5.0 mole equivalent relative to Compound (I).

Examples of an organic acid is N,N-dimethylformamide, diethyl ether, tetrahydrofuran, N,N-dimethyl acetamide and ethylene glycol dimethyl ether, and N,N-dimethylformamide is preferable.

Amount of water is not particularly limited. For example, the base is used as a 0.1% (w/w) to 30% (w/w), and preferably 1% (w/w) to 10% (w/w) aqueous solution of a base by adding water.

The reaction temperature is generally about −40 to 60° C., and preferably about −10 to 0° C. The reaction time is generally about 0.1 hour to 10 hours, and preferably about 0.5 hour to 4.0 hours.

This method is useful as a method for a large-scale production because Compound (IV) can be directly produced from Compound (I) for a quite short time and.

Thus-obtained Compound (IV) is subjected to the above Step 3 to give Compound (V). If necessary, Compound (V) can be isolated, preferably as crystals, by extracting, washing with water, crystallizing and the like.

Compound (V) can be easily converted to a pharmaceutical acceptable salt by the known procedures for forming salts.

Examples of a pharmaceutical acceptable salt of Compound (V) are salts or inner salts formed with an inorganic base, an ammonia, an organic base, a basic amino acid and the like. Examples of the inorganic base are alkaline metal such as Na, K, etc., alkaline earth metal such as Ca, Mg, etc. and examples of the organic base are trimethylamine, triethylamine, choline, procaine, ethanolamine, etc. Examples of the basic amino acid are lysine, arginine, ornithine, histidine. Preferable examples of salts of Compound (V) are an alkaline metal salt such as 2 Na salt and 3 Na salt. Compound (V) and the salts thereof may be solvates with water or alcohol.

As an additional embodiment of the present invention, a process for producing Compound (II) from the above Compound (VI) is described below.

(Step 1)

Compound (VII) is obtained by reducing a nitro group of Compound (VI) in the presence of Pd—C.

Weight ratio of Pd—C is about 0.01 to 0.2 equivalent and preferably about 0.05 to 0.1 equivalent relative to Compound (VI).

Examples of a solvent are water, ethyl acetate, acetonitrile, tetrahydrofuran, methanol and ethanol. Ethyl acetate or acetonitrile is preferable.

The reaction temperature is generally about −10 to 60° C. and preferably about −5 to 25° C.

The reaction time is generally about 0.5 hour to 10.0 hours and preferably about 1.0 hour to 5.0 hours.

According to this step, the reduction reaction can be performed without using TiCl$_3$ and the like which are undesirable for environment. Furthermore, the reaction using Pd—C is efficient because Pd—C can be recycled after the reaction.

Compound (VI) has an aldehyde group neighboring to a nitro group. Though a nitro compound having such aldehyde is generally reduced after protection of the aldehyde group (cf. Patent Literature 4), the nitro group was selectively reduced by this step without protection of the aldehyde group.

A solution of Compound (VII) is obtained by this step and Compound (VII) can be used in the following step without isolation. Therefore, the step is useful for manufacturing process.

(Step 2)

Compound (II) can be obtained by condensing Compound (VIII) with an amino group of Compound (VII) obtained in Step 1. Because Compound (VII) is very unstable, the pH value adjustment of the reaction solution is important in this reaction. This reaction efficiently proceeds when pH value is adjusted to 1 to 7, preferably 2 to 5 with acetic acid, sodium acetate and the like. Amount of Compound (VIII) can be reduced when the reaction is carried out in a two phase reaction.

Amount of Compound (VIII) is generally about 0.8 to 5.0 mole equivalent, and preferably about 1.0 to 1.5 mole equivalent relative to Compound (VI).

Examples of a solvent are water, acetic acid, ethyl acetate, acetonitrile, tetrahydrofuran, methanol and ethanol, and preferably ethyl acetate. The reaction temperature is generally about 0 to 40° C., and preferably about 0 to 15° C.

The reaction time is generally about 0.1 hour to 5.0 hours, and preferably about 0.5 hour to 1.5 hours. Methyl is preferable for R$^2$ in Compound (VIII).

When Steps 1 and 2 are continuously conducted in an organic solvent system, amount of Compound (VIII) in Step 2 can be considerably reduced compared with that in an aqueous system using TiCl$_3$.

(Step 2 Alternative Method)

Compound (II) can be obtained by reacting Compound (VII) obtained by Step 1 with Compound (VIII) in the presence of a base. N,N-dimethylaniline is preferable as a base to obtain the target Compound (II) in high yield and to suppress the formation of by-products.

Examples of a solvent are water, acetic acid, ethyl acetate, acetonitrile, tetrahydrofuran, methanol and ethanol, and acetonitrile is preferable.

The reaction temperature is generally about −10° C. to 40° C. and preferably about −10° C. to 10° C.

The reaction time is generally about 0.1 hour to 5.0 hours and preferably about 0.5 hour to 1.5 hours.

Amount of Compound (VIII) is generally about 0.8 to 5.0 mole equivalents and preferably about 1.0 to 1.5 mole equivalents relative to Compound (VI).

This alternative method has such merits as the target Compound (II) can be obtained in high yield, and the amount of Compound (VIII) can be decreased compared with that in aqueous system using TiCl$_3$.

Examples of a salt and a solvate of Compound (II) are the same as that of the above-mentioned Compound (V).

The present invention provides crystal of the above Compound (I-1). The crystal is exemplified by the one characterized by the following main peaks of diffraction angle measured by a powder X-ray diffraction.

2θ=5.760, 6.480, 9.580, 10.080, 14.720, 15.340, 15.740, 19.480, 20.280 degree.

X-ray diffraction conditions:

Cu Kα ray: 1.54 Å

Tube voltage: 40 kV

Tube current: 40 mA

The above crystal has high stability for preservation and high purity. When this crystal is isolated and used as an intermediate, a step for purification such as column chromatography can be omitted in the processes for producing Compound (I) or a salt thereof. Therefore, this crystal is very important for manufacturing processes of Compound (I).

The present invention provides a process for purification of Compound (V). More specifically, this provides a method for removing endotoxin when endotoxin is mixed with Compound (V). This method includes a step that Compound (V) obtained by the above method or the like is dissolved in an organic solvent, followed by washing the mixture with water.

A preferable organic solvent is exemplified by ethyl acetate.

Even if water used in this method includes about some tens to some hundreds EU/mL of endotoxin, this method gives a sufficient purification effect. Water is preferably purified water, and distilled water for injection is more preferable.

Endotoxin mixed with Compound (V) is transferred to an aqueous layer by washing an organic solution containing Compound (V) with water. This operation gives a considerably purification effect only at one time, and is preferably repeated twice or more. By this repetition, the content of endotoxin can be decreased to about 1% or less, preferably about 0.5% or less relative to before this operation. Therefore, this process for purification is preferable when Compound (V) or a salt thereof is used for an injection.

EXAMPLES

Examples of the present invention are illustrated below. Abbreviations in Examples mean as follows:

DME: Ethylene glycol dimethyl ether

AcOH: Acetic acid

DMF: N,N-dimethylformamide

THF: tetrahydrofuran

Reference Example 1

Synthesis of Compound (3)

-continued

Compound (1) (18.2 g, 36.4 mmol) was suspended in DME (182 mL) and acetic acid (18.2 g), and 25% aqueous solution of titanium trichloride (49.4 g, 80.1 mmol) was poured into the mixture. After the mixture was heated to 50° C. and reacted for 1 hour, it was concentrated under reduced pressure about to 120 g. Ethyl acetate (91 mL) and water (91 mL) were added to the concentrated mixture and an organic layer was separated. The precipitates in the organic layer were filtered off and the organic layer was washed with 10% brine (91 g). After the aqueous layer was extracted with ethyl acetate (91 mL), all of the organic layers were combined and concentrated under reduced pressure to 44.25 g. DME (68.3 mL) and acetic acid (3.3 g) were added to 22.13 g of the obtained concentrated mixture. Into the mixture was poured 21% aqueous solution of sodium nitrite (17.85 g, 54.3 mmol) and the mixture was reacted for 1 hour at 25 (+10, −5)° C. After the completion of the reaction, 16% aqueous solution of sodium hydroxide (33.74 g) was poured into the mixture and the mixture was reacted for 4 hours at 50° C. This reaction was performed with adding 16% aqueous solution of sodium hydroxide to keep pH value 13 or more (Total amount of 16% aqueous solution of sodium hydroxide: 39.68 g). After the reaction was completed, the mixture was allowed to cool to 25° C. and methanol (54.6 mL) was poured into the mixture to crystallize. After the mixture was neutralized with 7% hydrochloric acid (5.6 g), the mixture was filtered to obtain 6.13 g of Compound (3) as white crystals (yield: 69.4%).

Reference Example 2

Synthesis of Compound (8)

(Ac: acetyl, Et: ethyl)

(1) Synthesis of Compound (6)

To a suspension of Compound (4) (8.0 g, 16.5 mmol) in toluene (56 mL) were added ethylene glycol (2.0 g, 33.0 mmol) and pyridinium p-tolunenesulfonate (0.2 g, 0.8 mmol). The mixture was refluxed at 110° C. with removing water by Dean-Stark trap. After 2 hours, the reaction mixture was cooled to 90° C., and ethylene glycol (1.0 g, 16.5 mmol) was added. The mixture was refluxed at 110° C. for additional 3 hours to obtain a solution of Compound (5) in toluene. The solution was cooled to 70° C., and pyridine (5.2 g, 66.0 mmol) was added. Acetic anhydride (5.1 g, 49.5 mmol) and 4-dimethylaminopyridine (0.6 g, 5.0 mmol) were added, and the mixture was reacted at 80° C. for 2 hours. After the reaction was completed, the mixture was allowed to cool to room temperature, and methanol was poured. The mixture was stirred for 2 hours at 5° C. and washed with cooled methanol (24 mL) to obtain 8,3 g of Compound (6) (yield 88%).

(2) Synthesis of Compound (8)

Metallic lithium (3.5 g, 498.6 mmol) was dissolved in a liquid ammonia which was previously cooled to −50° C., and a solution of Compound (6) (47.0 g, 82.3 mmol) in THF (400 mL) was added dropwise to the mixture over 1 hour. After the solution was reacted at −50° C. for 1 hour, ethanol (236 mL) was poured and the mixture was warmed to remove ammonia. Water was poured into the mixture at 10° C. and 7% hydrochloric acid (545 g) was added dropwise. The solution was stirred for 1 hour at 5 to 10° C., and appeared crystals were collected by filtration and washed with 50% aqueous solution of acetonitrile and acetonitrile to obtain wet crystals of Compound (7) (42.6 g).

27.21 g of thus-obtained wet crystals and diethyl phosphonoacetic acid (22.7 g, 115.6 mmol) were dissolved in DMF (150 mL) and ethyl acetate (600 mL). The mixture was concentrated under reduced pressure to about 210 mL by removing water, 1,1'-carbonyl bis-1H-imidazole (17.0 g, 105.1 mmol) was added to the mixture, and the mixture was reacted for 1 hour at 70° C. After the reaction was completed, the mixture was allowed to cool to room temperature and ethyl acetate (450 mL) was poured. After a pH value of the mixture was adjusted to about 5 by adding 3.5% hydrochloric acid dropwise, water (23 mL) was added and an organic layer was separated. The organic layer was kept at 40° C. and partitioned between the organic layer and water (240 mL). The aqueous layer was extracted with ethyl acetate (150 mL). These organic layers were combined and ethyl acetate (300 mL) was added. The mixture was concentrated under reduced pressure to about 300 mL to crystallize. The mixture was cooled to 0 to 5° C., stirred for 1 hour and filtered to obtain 22.8 g of Compound (8) as white crystals (yield: 63%).

Figure 1:
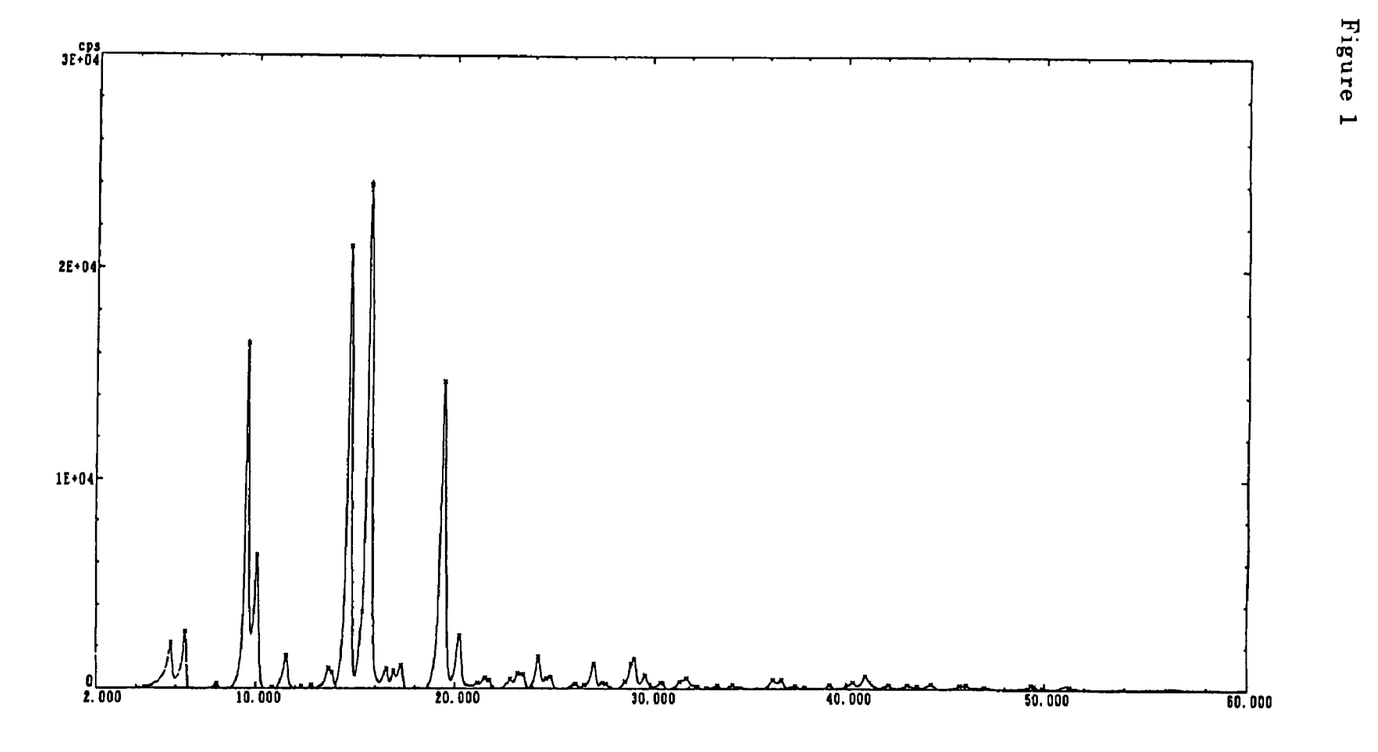
FIG. 1 shows powder X-ray diffraction pattern of Compound (5) obtained in Reference Example 1. A vertical axis shows a peak intensity and a horizontal axis shows a diffraction angle (2θ).

Powder X-ray diffraction chart of Compound (8) is shown as FIG. 1 and main peaks are shown as follows.

(X ray diffraction conditions: CuKα ray 1.54 Å, Tube voltage 40 mV, Tube current 40 mA)

| Diffraction angle (2θ, degree) | Spacing (d, Å) |
|---|---|
| 5.760 | 15.33071 |
| 6.480 | 13.62882 |
| 9.580 | 9.22449 |

-continued

| Diffraction angle (2θ, degree) | Spacing (d, Å) |
|---|---|
| 10.080 | 8.76802 |
| 14.720 | 6.01297 |
| 15.340 | 5.77131 |
| 15.740 | 5.62553 |
| 19.480 | 4.55309 |
| 20.280 | 4.37525 |

Example 1

Synthesis of Compound (9)

To a solution of Compound (13) (1.7 g, 10 mmol) in ethyl acetate (17 mL) was added 10% Pd—C (50% wet) (0.25 g) and hydrogenated for 5.5 hours at 15 to 20° C. at atmospheric pressure. The catalyst was filtered off and washed with ethyl acetate (8 mL). To thus-obtained solution of Compound (14) in ethyl acetate, an aqueous solution (33 mL) of sodium acetate (0.8 g) and acetic acid (3.3 mL) were added (pH 3.90) under ice-cooling. 3-methoxycarbonyl acrylate chloride (1.5 g) was added dropwise to the mixture under ice-cooling and the mixture was stirred for 50 minutes. The appeared crystals were collected by filtration, washed with water (20 mL) and ethyl acetate (5 mL) and dried to obtain 1.8 g of Compound (9) (yield: 72%).

Example 2

Synthesis of Compound (9)

Compound (13) (10.0 g, 59.8 mmol) and 10% Pd—C (2.08g, 52.1% wet, 10% (w/w)) were suspended in acetonitrile (200 mL) and the mixture was cooled below 0° C. The mixture was stirred for 1 hour or more with keeping below 5° C. with providing hydrogen at 4 kgf/cm² or less. Pd—C was filtered off and washed with acetonitrile to obtain a solution of Compound (14) in acetonitrile. N,N-dimethylaniline (6.53 g, 53.9 mmol) was added to thus-obtained solution and the mixture was added dropwise to a solution of 3-methoxycarbonyl acrylate chloride (10.7 g, 72.0 mmol) in acetonitrile (50 mL) which was previously cooled to −5° C. After the addition was completed, yellow solid (Compound (9)) was appeared. The reaction mixture was stirred for 30 minutes and water (100 mL) was added. The mixture was warmed to room temperature and allowed to stand for one day. After concentration under reduced pressure, the mixture was stirred for 1 hour under ice-cooling. Precipitated yellow solid was collected by filtration and washed with 1 mol/L hydrochloric acid and water to obtain Compound (7) as wet crude crystalline product. Thus-obtained product was suspended in a mixture of DMF (100 mL) and acetonitrile (50 mL) and dissolved at 40° C. After 0.66% aqueous solution of sodium hydrogencarbonate (302 g) was added dropwise to the solution to precipitate yellow solid of Compound (9), the mixture was cooled to room temperature and stirred for 1 hour. Precipitated yellow solid was collected by filtration and washed with water to obtain 12.3 g of pure product of Compound (9) (yield: 82.5%).

Example 3

Effect of a Base on an Acylation Reaction

As a base used for acylation, N,N-dimethylaniline, imidazole, pyridine, 2,6-lutidine, triethylamine and $Li_2CO_3$ were studied. In the reaction using N,N-dimethylaniline, Target Compound (9) was obtained in high yield and the formation of by-products was suppressed at a minimum compared with reactions using other bases.

| Base | HPLC peak area (%) Compound (9) | By-product A | By-product B | By-product C | yield (%) |
|---|---|---|---|---|---|
| None | 69.6 | 3.1 | — | — | 40.7 |
| N,N-dimethylaniline | 66.7 | 6.2 | — | 0.6 | 57.9 |
| imidazole | 62.6 | 1.6 | 1.4 | 1.7 | 47.1 |
| pyridine | 26.9 | 47.3 | 3.7 | 13.8 | — |
| 2,6-lutidine | 38.9 | 2.0 | 2.5 | 14.2 | 36.6 |
| $Li_2CO_3$ | 54.9 | 16.6 | — | — | 32.6 |

Example 4

Synthesis of Compound (12)

(Method 1) Compound (8) (12.6 g, 18,2 mmol), Compound (9) (5.0 g, 20.0 mmol) and lithium chloride (1.9 g, 45.5 mmol) were suspended in DMF (47.8 g) and the mixture was cooled to below 10° C. After DBU (1,8-diazabicyclo[5.4.6]undec-7-ene) (6.9 g, 45.5 mmol) was added, the mixture was warmed to room temperature and reacted for 20 hours to obtain a solution of Compound (10) in DMF. The solution was cooled to −5° C. and 4% aqueous solution of lithium hydroxide (37.7 g) was added dropwise to the mixture. The mixture was stirred 1 hour at −5° C. to obtain a solution of Compound (11) in DMF. The solution was warmed to 35° C., 35% hydrochloric acid (16.1 g) was added and the mixture was stirred for 1 hour at 45° C. After the reaction was completed, ethyl acetate (136 mL) and water (120 g) were added to the mixture and an organic layer was separated. After an aqueous layer was extracted with ethyl acetate, all of the organic layers were combined, washed with water. The organic layer was extracted with 5% aqueous solution of sodium hydrogencarbonate. After the aqueous layer was separated, ethyl acetate (160 mL) was added. A pH value of the mixture was adjusted to about 5 with 7% hydrochloric acid. The aqueous layer was extracted with ethyl acetate and all of organic layers were combined after washed with water. The combined organic layer was concentrated under reduced pressure, seed crystals of Compound (12) were added at 70° C. and the mixture was stirred for 1 hour. After crystallization, acetonitrile (52 g) was added, the mixture was gradually cooled to room temperature and stirred for 2 hours. The precipitated yellow solid was collected by filtration and washed with acetonitrile to obtain 9.3 g of Compound (12) (yield: 70%).

(Method 2) Compound (8) (25.20 g, 36.4 mmol) and Compound (9) (10.88 g, 43.7 mmol) were suspended in DMF (176 mL). To the mixture, lithium hydroxide (3.82 g, 91.0 mmol) was added and the mixture was reacted for 20 hours to obtain a solution of Compound (10) in DMF. After the solution was cooled to −5° C., 3% aqueous solution of lithium hydroxide (75.34 g) was added dropwise to the mixture and the mixture was stirred for 1 hour at −5° C. to obtain a solution of Compound (11) in DMF. The mixture was warmed to 35° C., 35% hydrochloric acid (28.4 g) was added, and the mixture was stirred for 1 hour at 45° C. After the reaction was completed, the mixture was partitioned between ethyl acetate (89 mL) and water (240 g). An aqueous layer was extracted with ethyl acetate and each of organic layers was washed with water. The organic layer was extracted with 5% aqueous solution of sodium hydrogencarbonate. An aqueous layer was separated and ethyl acetate (320 mL) was added. A pH value of the mixture was adjusted to about 5 with 7% hydrochloric acid and extracted. An aqueous layer was extracted with ethyl acetate and all of organic layers were combined after washed with water. One-fourth of the combined solution (corresponding to Compound (8) 6.30 g, 9.1 mmol) was concentrated, seed crystals of Compound (12) were added at 70° C. and the mixture was stirred for 1 hour. After crystallization, acetonitrile (26 g) was added, the mixture was gradually cooled to room temperature and stirred for 2 hours. Precipitated yellow solid was collected by filtration and washed with acetonitrile to obtain 4.8 g of Compound (12) (yield: 73%).

Example 5

Synthesis of Compound (12)

Compound (8) (3.46 g, 5 mmol) and Compound (9) (1.50 g, 6 mmol) were suspended in DMF (24.2 mL) and the mixture was cooled to below −5° C. To the mixture, 5.6% aqueous solution of lithium hydroxide (10.7 g, 25 mmol) was added dropwise and the mixture was reacted for 3.5 hours to obtain a solution of Compound (11) in DMF. The mixture was warmed to 5° C., 35% hydrochloric acid (3.39 g, 32.5 mmol) was added and the mixture was stirred for 2 hours at 45° C. After the reaction was completed, the mixture was allowed to cool to room temperature and ethyl acetate (44.6 g) and water (33.5 g) were added. After a pH value of the mixture was adjusted to about 5.5 with 10% aqueous solution of sodium hydroxide, an organic layer was separated. An aqueous layer was extracted with ethyl acetate and all of organic layers were combined after washed with water. The combined solution was concentrated under reduced pressure and crystallized at 70° C. Acetonitrile (14.9 g) was added to the mixture, the mixture was gradually cooled to room temperature and further to 0° C., followed by stirred for 1 hour. Precipitated yellow solid was collected by filtration and washed with acetonitrile to obtain 2.97 g of Compound (12) (yield: 81.4%).

Example 6

Compound (12) (3.11 g, yield: 85.3%) was obtained by similar methods of Example 5 except that Compound (II') wherein $R^3$ is hydrogen was used instead of Compound (9), 8.8% aqueous solution of sodium hydroxide (11.4 g, 25 mmol) was used as a base and the reaction time was for 2 hours.

Example 7

Method for Removing Endotoxin

Note: EU/mL Means a Concentration of Endotoxin.

Compound (12) (18. g) obtained in Example 4 (<0.3 EU/mL) was added to the mixture of ethyl acetate (40 mL, <1.2 EU/mL) and distilled water wherein the endotoxin concentration was previously adjusted to 120 EU/mL although distilled water was originally endotoxin-free (17 mL) and separated (120 EU/mL in aqueous layer). The organic layer was extracted with distilled water for injection (17 mL, endotoxin-free) (6 EU/mL in aqueous layer). The organic layer was subjected to additional extraction with distilled water for injection (17 mL) (0.6 EU/mL in aqueous layer). The organic layer was concentrated, ethyl acetate (25.5 mL, <1.2 EU/mL).was added and the mixture was concentrated. After acetonitrile (8.6 mL, <0.3 EU/mL) was added to the mixture at 70° C. and the mixture was stirred, it was gradually allowed to cool to room temperature. Precipitated yellow solid was collected by filtration and washed with acetonitrile (31 mL, <0.3 EU/mL) to obtain Compound (12) (1.5 g, <0.3 EU/mL).

INDUSTRIAL APPLICABILITY

Triterpene derivatives which are useful for an endothelin receptor antagonist and the like can be efficiently manufactured by the processes of the present invention. Additionally, the present invention provides a crystal of an intermediate which is useful for synthesis of the triterpene derivatives.

What is claimed is:

1. A process for preparation of Compound (V), a pharmaceutically acceptable salt or a solvate thereof, said process comprising the steps of:
   (Step 1) producing a solution containing Compound (III) by reacting Compound (I) with Compound (II) in the presence of lithium hydroxide in an organic solvent,
   (Step 2) producing a solution containing Compound (IV) by adding lithium hydroxide to the solution obtained by Step 1, and
   (Step 3) adding an acid to the solution obtained by Step 2,
   said process represented by the formula:

wherein $R^1$ and $R^2$ are each independently C1–C8 alkyl.

2. A process for preparation of Compound (V), a pharmaceutically acceptable salt or a solvate thereof, comprising conducting the following steps in sequence:
   (Step 1) dissolving Compound (I), Compound (II) and lithium hydroxide in an organic solvent,
   (Step 2) adding lithium hydroxide, and
   (Step 3) adding an acid,
   said process represented by the formula:

wherein $R^1$ and $R^2$ are each independently C1–C8 alkyl.

3. The process as claimed in claim 1 or 2, further comprising isolating Compound (V), a pharmaceutically acceptable salt or a solvate thereof.

4. The process as claimed in claim 1 or 2, wherein the organic solvent is N,N-dimethylformamide.

5. A process for preparation of Compound (II), a pharmaceutically acceptable salt or a solvate thereof, said process comprising the steps of:

(Step 1) producing a solution containing Compound (VII) by reducing Compound (VI) in the presence of Pd—C in mono-phase system, and (Step 2) reacting Compound (VII) in the solution obtained by Step 1 with Compound (VIII) in mono-phase system, said process represented by the formula:

wherein $R^2$ is C1–C8 alkyl.

6. The process as claimed in claim 5, wherein Step 2 is conducted at a pH value in the range from 1 to 7.

7. A process for preparation of Compound (II), a pharmaceutically acceptable salt or a solvate thereof, said process comprising the steps of:

29

(Step 1) producing a solution containing Compound (VII) by reducing Compound (VI) in the presence of Pd—C, and (Step 2) reacting Compound (VII) in the solution obtained by Step 1 with Compound (VIII) in the presence of N,N-dimethylaniline, said process represented by the formula:

30 wherein $R^2$ is C1–C8 alkyl.

8. A process for preparation of Compound (V), a pharmaceutically acceptable salt or a solvate thereof, said process comprising the steps of:

(Step 1) producing a solution containing Compound (IV) by reacting Compound (I) with Compound (II') in the presence of a base in an organic solvent and water, and (Step 2) adding an acid to the solution obtained by Step 1, said process represented by the formula:

(V)

wherein $R^1$ is C1–C8 alkyl and $R^3$ is hydrogen or C1–C8 alkyl.

9. A process for preparation of Compound (V), a pharmaceutically acceptable salt or a solvate thereof, comprising conducting the following steps in sequence:
(Step 1) dissolving Compound (I), Compound (II') and a base in an organic solvent and water, and
(Step 2) adding an acid
said process represented by the formula:

wherein $R^1$ is C1–C8 alkyl and $R^3$ is hydrogen or C1–C8 alkyl.

10. The process as claimed in claim 8 or 9, further comprising isolating Compound (V), a pharmaceutically acceptable salt or a solvate thereof.

11. The process as claimed in claim 8 or 9, wherein the base is lithium hydroxide, sodium hydroxide or potassium hydroxide.

12. A process for preparation of Compound (V), comprising removing endotoxin by dissolving Compound (V) according to claim 1 in an organic solvent and washing with purified water.

13. The process as claimed in claim 12, wherein the organic solvent is ethyl acetate.

14. The method claimed in claim 12 or 13, wherein endotoxin is not substantially included in the purified water.

* * * * *